March 28, 1950 J. D. BROWNELL Plant Pat. 928
ROSE PLANT
Filed Feb. 23, 1949
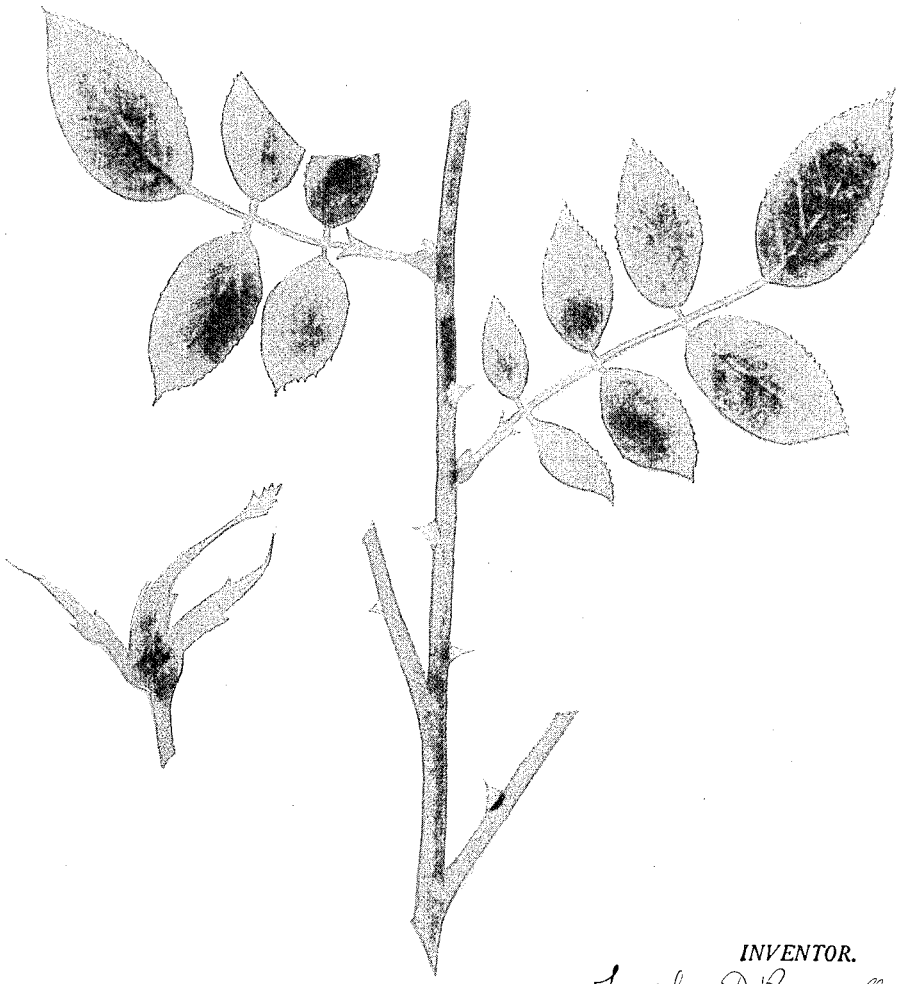
INVENTOR.
BY Josephine D. Brownell Patented Mar. 28, 1950 Plant Pat. 928

UNITED STATES PATENT OFFICE

928

ROSE PLANT

Josephine D. Brownell, Little Compton, R. I.

Application February 23, 1949, Serial No. 77,841

1 Claim. (Cl. 47—61)

My invention relates to roses and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by cross pollenation, which can be and has been asexually reproduced.

My new rose is new as to the following characteristics and especially as to their joint association with the characteristics inherited from *Rosa wichuraiana,* of hardiness, or immunity from serious injury on account of cold temperatures prevailing in certain parts of the northern United States;

The yellow to pink shades (ordinary dictionary definition) of its petals, in combination with the unique brilliance thereof and their tendency to hold these colors under exposure.

The novelty and variation within certain definite limits of the form of the bloom, its character of holding that form for a long time, and the petalage of the flowers;

Its character of fragrance;

Its unusual abundance of flowers, notably after early bloom time and until frost;

The intensity of its remontant and everblooming or reblooming character;

Its character of ascending in height by recurrent branching and progressively longer stems from the base in some instances long enough to be classified as canes;

The character of producing many seven leafleted leaves; which character seldom has obtained on hybrid teas not having *Rosa wichuraiana* ancestry, but frequently obtains on flower stems of descendents of *Rosa wichuraiana* of the dwarf reblooming type;

And especially its characteristic of partial freedom from premature defoliation by blackspot, under certain definite conditions of exposure, without any cultural control.

In the accompanying drawing forming a part of this specification I have shown my new rose in its natural colors, that is, as near as is possible to do so artificially.

My new rose is otherwise described as follows:

*Essential information*

Type: Hybrid tea, *Rosa wichuraiana* hybrid, dwarf, to ascending to tall to climber, for garden display, cut flower and forcing or growing under glass.

Class: Hybrid tea crossed with *Rosa wichuraiana,* further restricted by originator to include only those varieties that can survive moderately low sub-zero temperatures.

Breeding: This variety was produced and bred by me and under my direction by propagation and cross pollenation.

It came into being as a seedling grown from a seed born on a plant of "Pink Princess," Plant Patent 459, and the pollen parent of my new rose was "Shades of Autumn," Plant Patent 542.

The pollenation that fertilized the seed that grew into my new rose, as well as the pollenation that produced its seed parent were directed by me and were performed by emasculating flowers and placing thereon a bag protecting from self and foreign pollen. These bags were later removed and the flowers were hand pollenated with a camel's hair brush and the bags immediately replaced. The date of this pollenation was July 17, 1944.[1] The seed was planted under my direction on December 21, 1944, and the date of the first flower was August 11, 1945.

The plant and flower seemed to me to be of unusual merit and I have since made and directed extensive propagations and tests thereof.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August in 1946–8 inclusive and the characters have successively reproduced, true to the original seeding.

*Flower*

Habit: It blooms out of doors in Little Compton, beginning about three days prior to the average beginning time of commercial hybrid teas and continues relative to growth of the plant until frost.

Flowers borne: Often one and frequently two or three and occasionally more on each stem, in the usual hybrid tea type of cluster. The pedicels and peduncles are medium large in diameter and medium in length, erect, stiff, almost smooth, free from large prickles and bristles but with a few very small prickles varying to small hairs. Stems are long, diameter medium to large and notably stiff and rigid.

Quantity of bloom: Free, being cumulative in quantity from year to year as the plant increases in size, flowering through the summer.

Fragrance: Distinctive, pleasing China tea in combination with that of *Rosa wichuraiana,* under favorable environment.

[1] This and other dates herein are approximate.

Bud: Neck normal as described, opens well, being little to not at all affected by hot or wet weather or both, as to color and form, except at very high temperatures the color is less intense and the form of the petals is less recurled.

Before the calyx breaks the size is medium, form moderately pointed, frequently with one or more sepals having foliaceous parts extending beyond the apex of the calyx up to about three quarters of an inch, the number and size of the foliaceous parts being variable and frequently having one or more narrow, pointed, serrate appendages on each side of the sepals, otherwise the sepals are usually normal and regular, tapering to lanceolate at their apex, turning back nearly perpendicular to the pedicel as the bud opens.

Color [2] of the bud is bicolored and variable in pattern. The tip is Carmine No. 21/1 to No. 21/2 blending downward irregularly with Orange 12/2 and thence to Maize Yellow 607 and 607/1.

As the flower opens the inner side of petals is same colors as outer surface. Both sides gradually fade to Azalea Pink No. 618/1 and 618/2. The lower surfaces change toward Saffron Yellow No. 7/3.

The flower is usually 4 to 5½ inches in diameter when fully open, infrequently more or less, petals average around 75, frequently some smaller petals and petaloids in the center, variable in number.

The flower opens high centered, formal, recurled, not usually showing stamens and pistils. The several outer rows of petals are variable from obovate to ovate, several rows of the inner petals are much narrower and frequently are folded to about 90 to 110 degrees along a center vertical axis. Texture is medium to thick and leathery; both sides brilliant; with slight veining which is not prominent. The time of opening in favorable conditions is three to seven days.

The petals are substantial and after about eight to ten days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

Reproductive organs:

*Stamens*, quantity variable, around medium or slightly uneven lengths.

*Anthers*, Light Salmon Orange (reference to Ridgway).

*Filaments*, nearly Mustard Yellow (reference same).

*Pistils* are several of slightly uneven length, averaging around one-half inch long.

*Ovaries* are usually all inclosed.

*Hips* frequently develop to ovoid to globular, color, comparable with under side of leaves with variable colored overlay on the side exposed to the sun, moderately smooth; walls, thin, fleshy, medium in size.

*Sepals* are persistent and break off easily.

*Plant*

Foliage: Is abundant, of compound leaves of three to five leaflets near the flower, five leaflets

[2] The following color references are to the British Horticultural color chart unless otherwise noted.

lower down the stem and frequently seven leaflets in the middle of the stem and nearer the base. Size of leaflets medium, averaging in size a little larger than half way between the average hybrid tea and the *Rosa wichuraiana* leaflets. As the plants develop in size some of the leaflets develop to twice the size described above. Form of leaflets usually ovate with apex moderately acute, base rounded frequently slightly acute. In some instances with the circumference on one side of the petiolule out of alignment with the other side by about one-sixteenth of an inch or less, margins with pointed serrations, petiolules short.

The color of the upper side of the leaflets is slightly variable Scheeles Green No. 860/2 to Spinach Green No. o960/3. The under side is nearly Williow Green, ooo862/1.

The rachises are medium, moderately narrow to slender, upper side smooth except some very short hairs on edges. Under side moderately smooth, usually 3 to 5 short prickles.

Stipules are medium to long, averaging about three-quarters of an inch long, with sharp points, the upper edges of which normally form an angle of about 80 degrees.

Habit, dwarf, becoming bushy to tall; upright, compact, more cumulative in growth from year to year than the normal hybrid tea rose plant, by stems from the base and by rebranching and growth and enlargement and extension of the stems from the base. The growth is moderately free at first, developing more rapidly after one or two years under favorable vegetative opportunity.

Color of mature stems is the same as that of the upper surface of mature leaves, shading variously lighter and also with overlay of Indian Lake variable in intensity.

Prickles, several, frequently two to four between leaves, averaging in length about one-quarter inch, shading from Indian Lake to lighter at the base, turning lighter throughout and later to nearly colorless. Hairs few on upper portions of stems.

Winter resistance: A notable characteristic of this new rose is its resistance to moderate sub-zero temperatures in combination with its hybrid tea character and its *Rosa wichuraiana* ancestry. This variety with grafted bud and plant above entirely exposed above ground to moderate sub-zero temperatures survived and bloomed normally the following season. The word temperature herein refers to the Fahrenheit scale.

Comparisions: The hybrid tea Peace (Plant Patent 591) compares in some respects with my new rose, especially as to the color pattern, except my rose has many more petals, the petals are smaller and the edges show more and deeper pink. My rose averages about ¾ of an inch smaller in size. The wood of my rose is notably resistant to exposure to cold.

I know of no *Rosa wichuraiana* hybrid tea with which to compare it.

I claim:

The new rose plant variety, substantially as shown and described, characterized by its color pattern, form and color and its Wichuraiana traits.

JOSEPHINE D. BROWNELL.

No references cited.